(12) United States Patent
Connolly

(10) Patent No.: US 9,675,782 B2
(45) Date of Patent: Jun. 13, 2017

(54) CATHETER PULL WIRE ACTUATION MECHANISM

(71) Applicant: Medtronic Vascular, Inc., Santa Rosa, CA (US)

(72) Inventor: Colm Connolly, Westmeath (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 535 days.

(21) Appl. No.: 14/050,694

(22) Filed: Oct. 10, 2013

(65) Prior Publication Data

US 2015/0105809 A1 Apr. 16, 2015

(51) Int. Cl.
*A61M 25/092* (2006.01)
*A61M 25/01* (2006.01)
*A61B 17/00* (2006.01)

(52) U.S. Cl.
CPC .... *A61M 25/0147* (2013.01); *A61M 25/0136* (2013.01); *A61B 2017/00323* (2013.01)

(58) Field of Classification Search
CPC .............. A61M 25/01; A61M 25/0133; A61M 25/0136; A61M 25/0147; A61M 25/015; A61M 25/0177
USPC ............... 604/95.04, 523, 528; 600/433–435
See application file for complete search history.

(56) References Cited

U.S. PATENT DOCUMENTS

| | | | |
|---|---|---|---|
| 5,125,896 A * | 6/1992 | Hojeibane | A61B 5/0422 604/95.04 |
| 5,275,151 A | 1/1994 | Shockey et al. | |
| 5,487,757 A * | 1/1996 | Truckai | A61B 18/1492 604/264 |
| 5,562,619 A | 10/1996 | Mirarchi et al. | |
| 5,865,800 A * | 2/1999 | Mirarchi | A61B 17/221 604/95.04 |
| 6,554,794 B1 * | 4/2003 | Mueller | A61B 17/3478 604/528 |
| 6,663,588 B2 * | 12/2003 | DuBois | A61M 25/0147 604/95.01 |
| 7,842,025 B2 | 11/2010 | Coleman et al. | |
| 7,881,809 B2 * | 2/2011 | Rashidi | A61B 18/1492 600/374 |
| 7,935,108 B2 | 5/2011 | Baxter et al. | |
| 8,641,664 B2 * | 2/2014 | Kirschenman | A61M 25/0067 604/95.04 |
| 9,308,349 B2 * | 4/2016 | Rezac | A61M 25/0136 |
| 2006/0264819 A1 * | 11/2006 | Fischer | A61M 25/0136 604/95.04 |
| 2012/0029334 A1 * | 2/2012 | Tegg | A61M 25/0136 600/373 |

(Continued)

*Primary Examiner* — Ahmed Farah

(57) ABSTRACT

A catheter has an elongate tubular component that defines a pull wire lumen, which extends along at least a portion of a length thereof. A pull wire extends within the pull wire lumen with a distal end of the pull wire being secured near a distal end of the catheter. The catheter includes a pull wire actuation mechanism slidably disposed thereon that is operably coupled to a proximal end of the pull wire. The pull wire actuation mechanism includes a first or upper housing portion that is longitudinally translatable in a first direction relative to the guide catheter and a second or lower housing portion that is longitudinally translatable in an opposite, second direction relative to the catheter to actuate the pull wire and selectively operate the distal end thereof.

20 Claims, 8 Drawing Sheets

(56) References Cited

U.S. PATENT DOCUMENTS

| | | | | |
|---|---|---|---|---|
| 2012/0203169 A1* | 8/2012 | Tegg | ....................... | B29C 65/02 |
| | | | | 604/95.04 |
| 2013/0172814 A1* | 7/2013 | Olson | ............... | A61M 25/0155 |
| | | | | 604/95.04 |
| 2014/0276594 A1* | 9/2014 | Tanner | .............. | A61M 25/0147 |
| | | | | 604/506 |

* cited by examiner

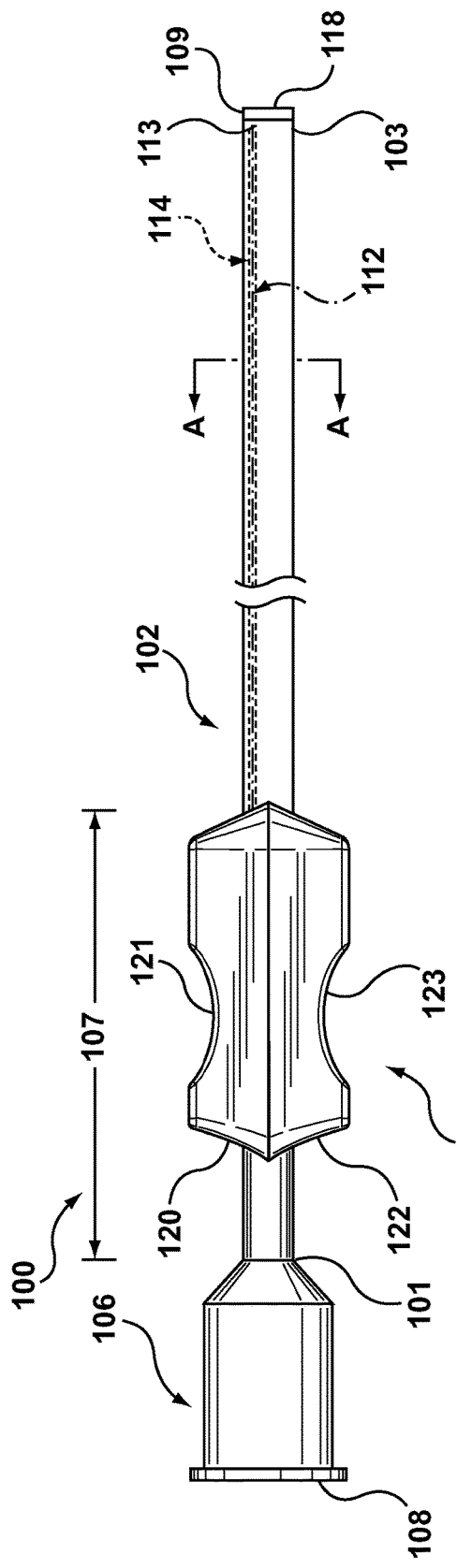
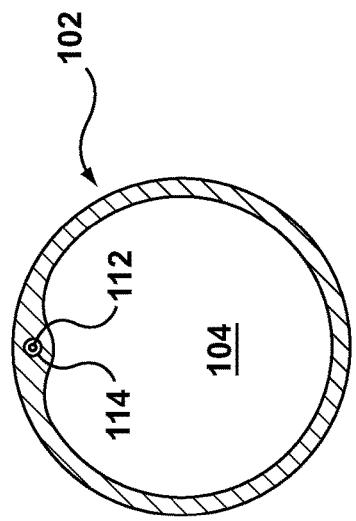
FIG. 1
FIG. 1A

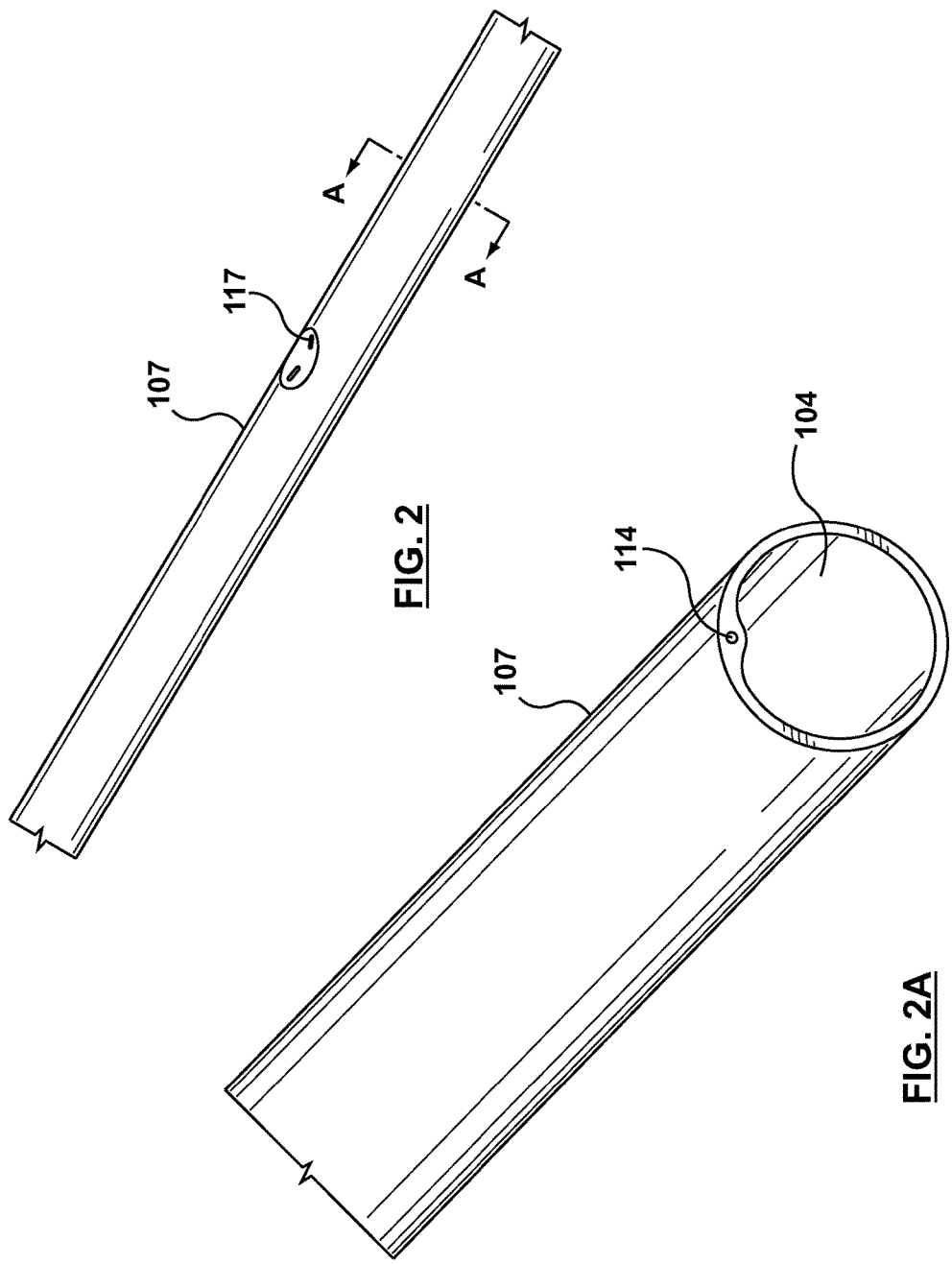

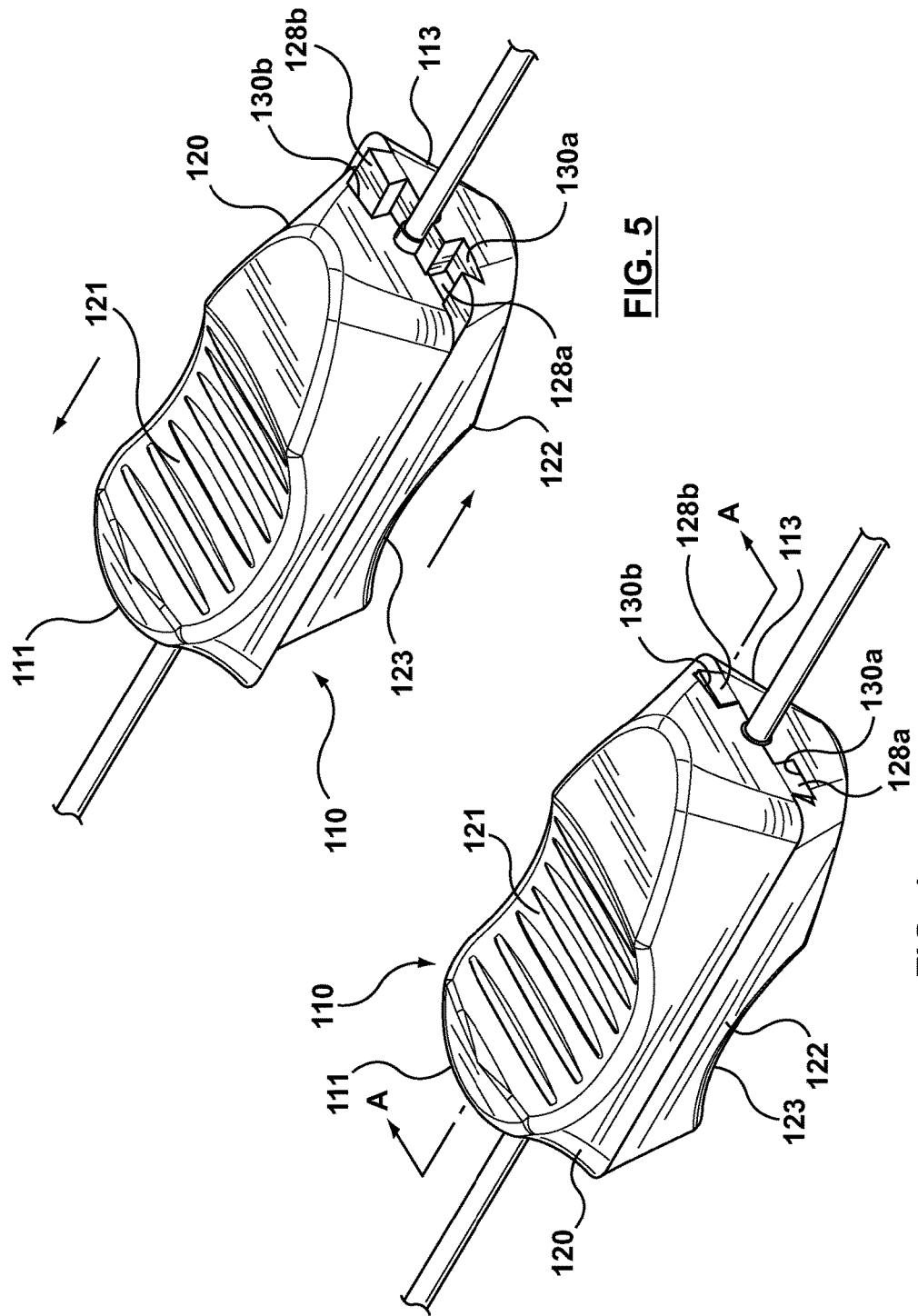

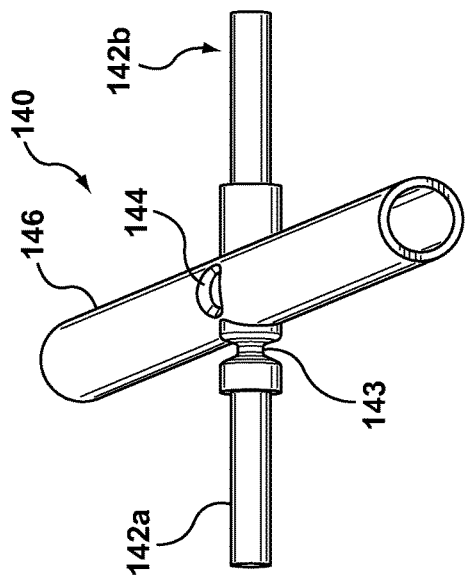
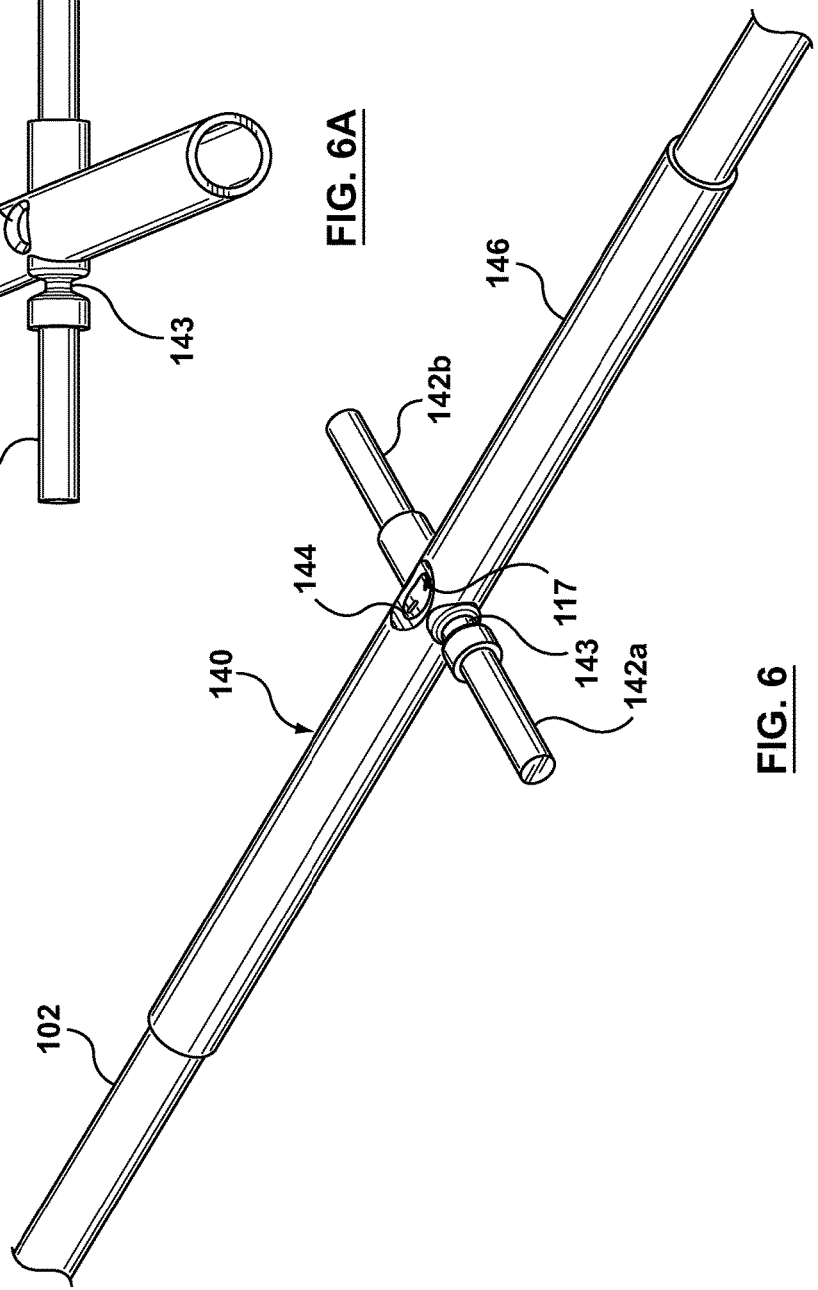

CATHETER PULL WIRE ACTUATION MECHANISM

FIELD OF THE INVENTION

The invention relates generally to pull-wire actuable catheters and, more particularly, to a pull wire actuation mechanism for selectively transforming a catheter between various configurations.

BACKGROUND OF THE INVENTION

Numerous types of catheters are actuatable by use of one or more pull wires incorporated therein. Among these types of catheters are steerable radio frequency ablation catheters having tips that are deflected in transverse directions by applying tension to one or more pull wires attached proximate the distal tips. Another type of pull-wire actuated catheter has a basket that can be radially expanded for such procedures as endocardial mapping and/or ablation, rotational atherectomy, thrombectomy, or embolectomy. Yet another type of pull-wire actuated catheter is a multi-electrode renal denervation catheter capable of deforming into a helical shape or other complex bend to achieve apposition against the inner wall of a renal blood vessel. While the pull wire actuation mechanism of the current technology may be employed with any of various types of catheters, the description herein will discuss, without being limited thereto, a PTCA guiding catheter having a deflectable tip.

A stenosis, lesion, or narrowing of a blood vessel such as an artery may comprise a hard, calcified substance and/or a softer thrombus material. There have been numerous interventional catheterization procedures developed for the treatment of stenoses in arteries. One of the better-known procedures is percutaneous transluminal coronary angioplasty (PTCA). According to this procedure, a narrowing in a coronary artery can be expanded by positioning and inflating a dilatation balloon across the stenosis to enlarge the lumen and re-establish acceptable blood flow through the artery. Additional therapeutic procedures may include stent deployment, atherectomy, and thrombectomy, which are well known and have proven effective in the treatment of such stenotic lesions.

In cases where the lesion targeted for treatment is located distant from a convenient vascular access location, the therapeutic procedure typically starts with the introduction of a guide catheter into the cardiovascular system from an easily reachable site, such as through the femoral artery in the groin area or other locations in the arm or neck. The guide catheter is advanced through the arterial system until its distal end is located near the stenosis that is targeted for treatment. During PTCA, for example, the distal end of the guide catheter is typically inserted only into the ostium, or origin of a coronary artery. A guidewire is advanced through a main lumen in the guide catheter and positioned across the stenosis. An interventional medical device or treatment catheter, such as a balloon dilatation catheter, is then slid over the guidewire until the dilatation balloon is properly positioned across the stenosis. The balloon is inflated to dilate the artery. To help prevent the artery from re-closing, a physician can implant a stent inside the dilated portion of the artery. The stent is usually delivered to the artery in a compressed shape on a stent delivery catheter and is expanded by a balloon to a larger diameter for implantation against the arterial wall.

Guide catheters typically have a pre-shaped distal curve that is sized and shaped for positioning in a main vessel to orient or direct a distal tip of the catheter into the ostium of a branch vessel. PTCA guide catheters, for example, may have a pre-shaped curve that fits within the aortic root and/or the ascending aorta for positioning the distal end of the catheter near or within the ostium of a left or right native coronary artery or a bypass graft, depending on the curve selected. Many guide catheter pre-shaped distal curves are also sized and shaped to span the width of the main vessel to support branch vessel intubation from a main vessel wall location that is contralateral, or generally opposite to the ostium of the branch vessel.

In some situations, the pre-shaped distal curve of the guide catheter may not be the correct curvature needed for the placement of the distal tip at a target site within the patient's cardiovascular system. When the pre-shaped distal curve is not a perfect match for the patient's anatomy often times the clinician will choose to withdraw the guide catheter from the patient's body and replace it with a guide catheter having a different distal curvature. Such a re-catheterization process not only increases the time required for the interventional procedure but also adds further arterial trauma. In some circumstances to avoid the steps of removing the less than optimally curved guide catheter and tracking a subsequent guide catheter with a more suitable pre-shaped distal curvature to the target site, the clinician may choose to use the indwelling less suitable guide catheter even though coaxial seating of the guide catheter distal tip within an ostium of a vessel may be very difficult or never achieved.

In order to address the ostium or aortic root geometry that may be encountered during an interventional procedure, medical device manufactures make and sell a vast number of guide catheters having a variety of pre-shaped distal curvatures, which consequently results in hospitals and clinics routinely maintaining inventories of a variety of guide catheters having various pre-shaped distal curvatures. In order to reduce the need to manufacture and inventory a vast number of guide catheters having various pre-shaped distal curvatures while still meeting the curvature needed for a particular interventional procedure, there remains a need in the art for a guide catheter that may be tracked to a target site within the patient's vasculature that once positioned has a distal portion or segment with a curvature that can be selectively changed to match the geometry of the target site.

BRIEF SUMMARY OF THE INVENTION

In accordance with an embodiment hereof, a catheter is disclosed having an elongate shaft or tubular component that defines a pull wire lumen, which extends along at least a portion of a length thereof. A pull wire extends within the pull wire lumen with a distal end of the pull wire being secured near a distal end of the catheter. The catheter includes an actuation mechanism slidably disposed thereon that is operably coupled to a proximal end of the pull wire. The actuation mechanism includes a first or upper housing portion that is longitudinally translatable in a first direction relative to the catheter and a second or lower housing portion that is longitudinally translatable in an opposite, second direction relative to the catheter to actuate the pull wire and selectively deflect the distal end thereof.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of a catheter in accordance with an embodiment hereof shown in a straight configuration.

FIG. 1A is a cross-sectional view of the catheter shown in FIG. 1 taken along line A-A.

FIG. 2 is a perspective view of a proximal portion of a shaft component of the catheter shown in FIG. 1.

FIG. 2A is a cross-sectional view of the shaft component proximal portion as shown in FIG. 2 taken along line A-A.

FIG. 4 is a perspective view of the actuation mechanism of FIG. 3 in a first configuration with first and second housing portions aligned.

FIG. 5 is a perspective view of the actuation mechanism of FIG. 3 in a second configuration with the first housing portion proximally displaced and the second housing portion distally displaced relative to the remainder of the catheter.

FIG. 6 is a perspective view of a proximal portion of a shaft component of the catheter shown in FIG. 1 with a bushing mounted thereon.

FIG. 6A is a perspective view of the bushing of FIG. 6 removed from the shaft component proximal portion.

DETAILED DESCRIPTION OF THE INVENTION

Figure 3:
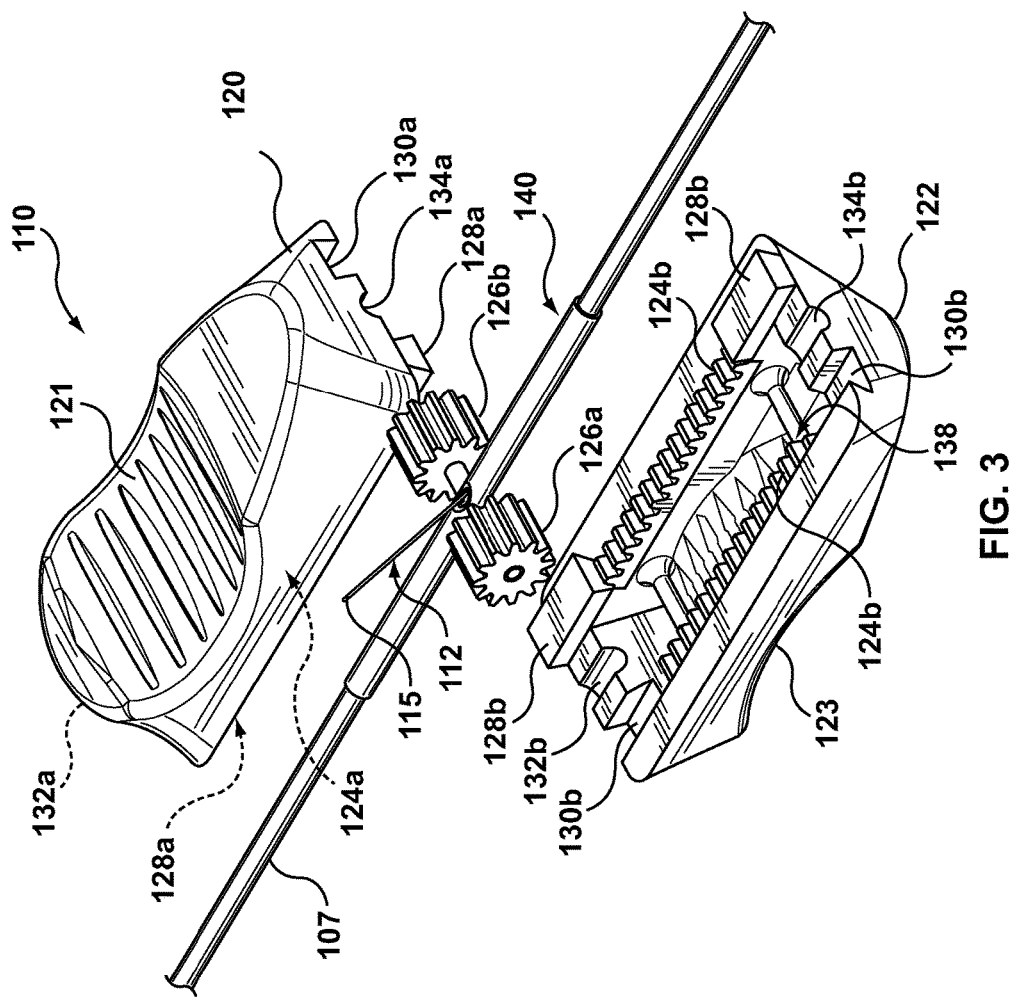
FIG. 3 is an exploded view of an actuation mechanism of the catheter shown in FIG. 1.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of embodiments hereof are in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

FIG. 1 is a side view of a catheter 100 in accordance with an embodiment hereof, with FIG. 1A depicting a cross-sectional view thereof taken along line A-A in FIG. 1. Catheter 100 includes an elongate shaft or tubular component 102, an elongate pull wire 112 extending within shaft component 102, and an actuation mechanism 110 slidably disposed on shaft component 102 and operably coupled to pull wire 112 for selectively deflecting a distal end 103 of shaft component 102. With further reference to FIGS. 2 and 2A that show shaft component 102 before assembly with the remainder of catheter 100, shaft component 102 defines a central lumen 104 (e.g. for use of catheter 100 as a guide catheter) from a proximal end 101 to distal end 103 thereof and a pull wire lumen 114 from a pull wire port 117 within a proximal portion 107 of the shaft component to the shaft component distal end 103. Pull wire lumen 114 is formed to longitudinally extend within a wall of shaft component 102 in parallel with central lumen 104 and is sized to slidably receive pull wire 112 therein. More particularly, a distal end 113 of pull wire 112 is secured or anchored within pull wire lumen 114 proximate to shaft component distal end 103 and a remaining length of pull wire 112 is slidably disposed to extend through pull wire lumen 114 and exit therefrom via pull wire port 117 to enter into actuation mechanism 110. A proximal end 115 of pull wire 112 is anchored within the actuation mechanism 110 as explained in detail below with reference to FIGS. 3 and 4A.

Shaft component proximal end 102 extends out of the patient and is coupled to a hub or Luer fitting 106 that defines a proximal port 108 of guide catheter 100, which is in fluid communication with central lumen 104. An atraumatic tip 109 is attached to shaft component distal end 103 and defines a distal port 118 of guide catheter 100, which is in fluid communication with central lumen 104. In an embodiment, tip 109 is formed of a radiopaque material or includes a radiopaque marker band proximate thereto in order to aid in visualization of the guide catheter tip under fluoroscopy. As would be understood by one or ordinary skill in the art, central lumen 104, proximal port 108 and distal port 118 of guide catheter 100 are sized to slidably receive a treatment catheter or other interventional medical device (not shown) there through. In embodiments hereof, guide catheter 100 may be a 5F-8F guide catheter with each of central lumen 104, proximal port 108 and distal port 118 having a working diameter of 0.058 inch to 0.090 inch.

With reference to the exploded view of the pull wire actuation mechanism 110 of guide catheter 100 shown in FIG. 3, the actuation mechanism 110 defines an interior within which pull wire proximal end 115 is received to be operably coupled thereto, as described in detail below. Pull wire actuation mechanism 110 includes a first or upper housing portion 120 that is longitudinally translatable in a first direction relative to shaft component 102 and a second or lower housing portion 122 that is longitudinally translatable in an opposite, second direction relative to shaft component 102 to actuate pull wire 112. Each of first and second housing portions 120, 122 is an outer casing of actuation mechanism 110 having a respective engagement surface 121, 123 that is configured to be engaged by a respective digit of a user's hand for longitudinally translating the first and second housing portions 120, 122 relative to each other. In order to facilitate their relative movement, first and second housing portions 120, 122 are slidably engaged with each other by a respective pair of linear slides 128a, 128b that are received within an opposing and corresponding respective pair of grooves 130a, 130b. In the embodiment shown in FIGS. 3, 4 and 5, linear slides 128a, 128b are shaped as dovetail slides but in another embodiment may be a pair of rectangular, circular, hemispherical or other shaped slides without departing from the scope hereof. First and second housing portions 120, 122 also include respective proximal shaft bearing surfaces 132a, 132b and distal shaft bearing surfaces 134a, 134b for slidably engaging shaft component 102. In the embodiment shown in FIG. 3, the proximal and distal shaft bearing surfaces are hemicylindrical shaped to match the external shape of shaft component 102. Accordingly, first and second housing portions 120, 122 are slidably coupled to proximal portion 107 of shaft component 102 with the shaft component being received through the interior of first and second housing portions 120, 122 between the opposing proximal and distal bearings surfaces defined thereby.

In order to synchronize or otherwise correlate the relative movement between the first and second housing portions 120, 122 of actuation mechanism 110, each of first and second housing portions 120, 122 also includes a respective pair of longitudinally-extending toothed rack segments 124a, 124b for engaging a pair of pinion gears 126a, 126b, which are disposed on a tubular bushing 140 within the interior of the actuation mechanism 110. Bushing 140 is a metallic tubular structure, which in FIG. 6A is shown removed from guide catheter 100 and in FIG. 6 is shown in a preassembly configuration with shaft component 102 extending therethrough. Bushing 140 is fixed to shaft component proximal portion 107, such as by being crimped or glued thereto, such that a side opening 144 of the bushing overlays or permits access to pull wire port 117. Bushing 140 includes a tubular main body 146 with transverse shafts 142a, 142b extending therefrom and on which respective pinion gears 126a, 126b are rotatably disposed. More particularly, each pinion gear 126a, 126b is configured to freely rotate clockwise or counterclockwise about its respective transverse shaft 142a, 142b by engagement with respective toothed rack segments 124a, 124b of first and second housing portions 120, 122. The ability to rotate in either direction permits the pinion gears to accommodate relative movement between first and second housing portions 120, 122 in opposite directions along shaft component 102, i.e., counterclockwise rotation permits first housing portion 120 to move proximally while second housing portion 122 moves distally and clockwise rotation permits first housing portion 120 to move distally while second housing portion 122 moves proximally. Transverse shaft 142a of bushing 140 also includes a turned groove 143 at the juncture with main body 146 over which a diagonal segment of pull wire 112 that crosses from first housing portion 120 to second housing portion 122, as described below, is disposed.

Figure 4A:
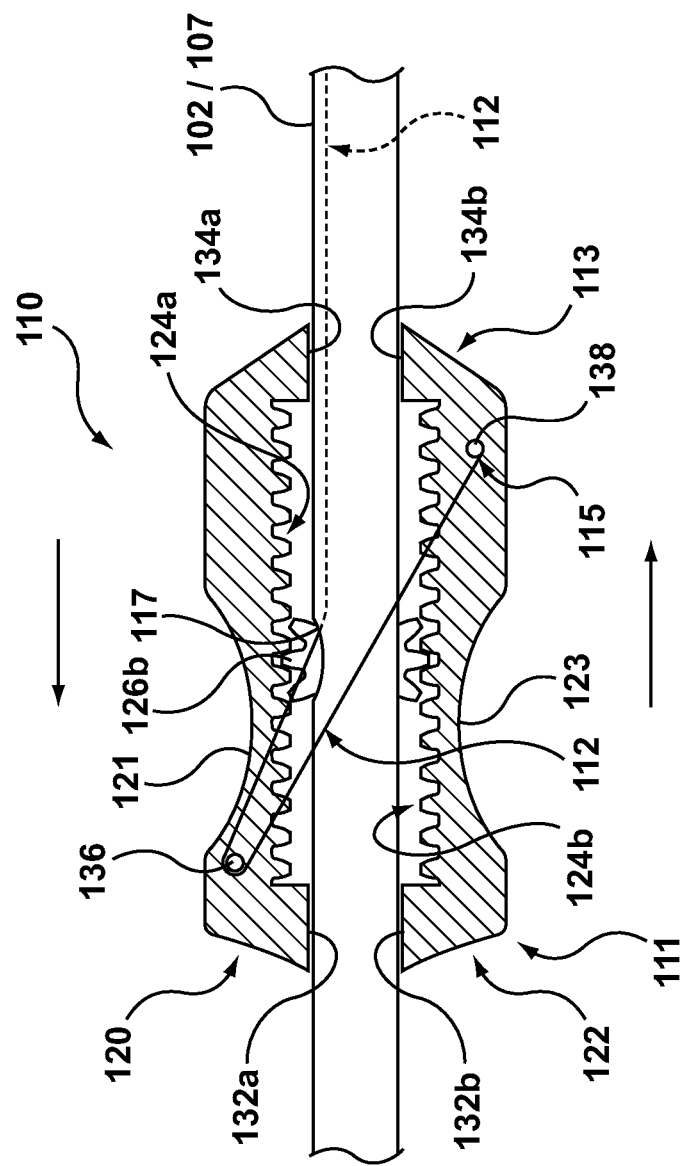
FIG. 4A is a sectional view of the actuation mechanism as shown in FIG. 4 taken along line A-A.
Figure 7:
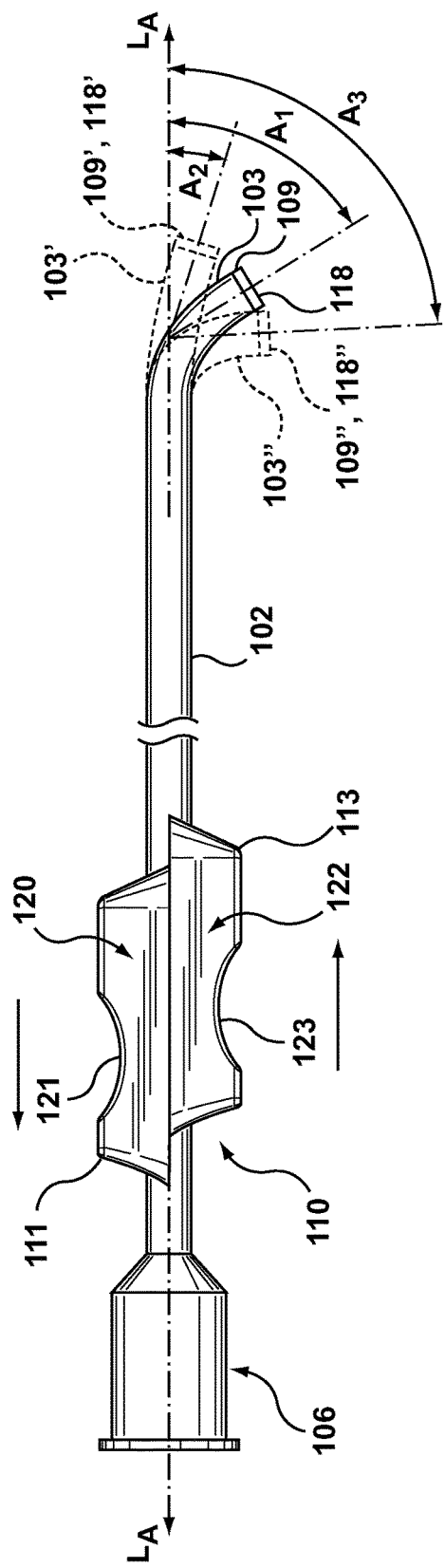
FIG. 7 is a side view of the catheter of FIG. 1 shown in a deflected configuration.

FIG. 4 depicts pull wire actuation mechanism 110 in a first configuration with first and second housing portions 120, 122 aligned, such that pull wire 112 is not tensioned thereby and guide catheter 100 is in the undeflected, straight configuration shown in FIG. 1. FIG. 4A depicts a sectional view of actuation mechanism 110 taken along line A-A of FIG. 4. With reference to FIG. 4A, pull wire 112 slidably extends from shaft component 102 through pull wire port 117, as well as bushing side opening 144, into the interior of actuation mechanism 110 where it wraps around a pulley pin or component 136 disposed within first housing portion 120 at or near a proximal end 111 of actuation mechanism 110 with the pull wire proximal end 115 being fixedly attached at an anchor point 138 within second housing portion 122 at or near a distal end 113 of actuation mechanism 110. When the first or upper housing portion 120 is proximally translated relative to shaft component 102 while the second or lower housing portion 122 is distally translated relative to shaft component 102, such that the actuation mechanism is in a second configuration shown in FIG. 5, pull wire 112 is simultaneously pulled proximally by pulley component 136 of first housing portion 120 while the proximal end 115 of pull wire 112 is being pushed distally at anchor point 138 of second housing portion 122. The simultaneous proximal and distal movement of pull wire 113 provided by actuation mechanism 110 results in a tensioning of pull wire 112 that applies a proximal force for deflecting guide catheter distal end 103 to an angle $A_1$ from a longitudinal axis $L_A$ of the guide catheter such that the guide catheter achieves a deflected configuration as shown in FIG. 7.

The amount of relative translation between first and second housing portions 120, 122 may be selectively varied, i.e., incrementally increased or decreased, to achieve various angles of defection of guide catheter distal end 103. For instance, less relative translation between first and second housing portions 120, 122 may result in a lesser angle of deflection $A_2$ at the distal end of guide catheter 100, such that guide catheter 100 can achieve the deflected configuration depicted by distal end 103' and tip 109' shown in dashed lines in FIG. 7. Conversely, a greater relative translation between first and second housing portions 120, 122 may result in a greater angle of deflection $A_3$ at the distal end of guide catheter 100, such that guide catheter 100 can achieve the deflected configuration depicted by distal end 103" and tip 109" shown in dashed lines in FIG. 7.

Figure 8A:
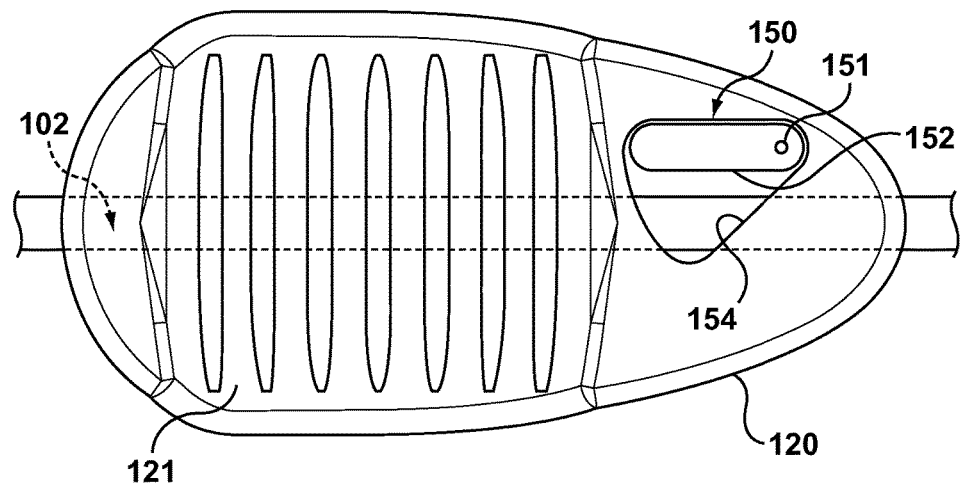
FIGS. 8A and 8B are top views of an actuation mechanism in accordance with an embodiment hereof that depict a locking mechanism in an unlocked and locked position, respectively.
Figure 8B:
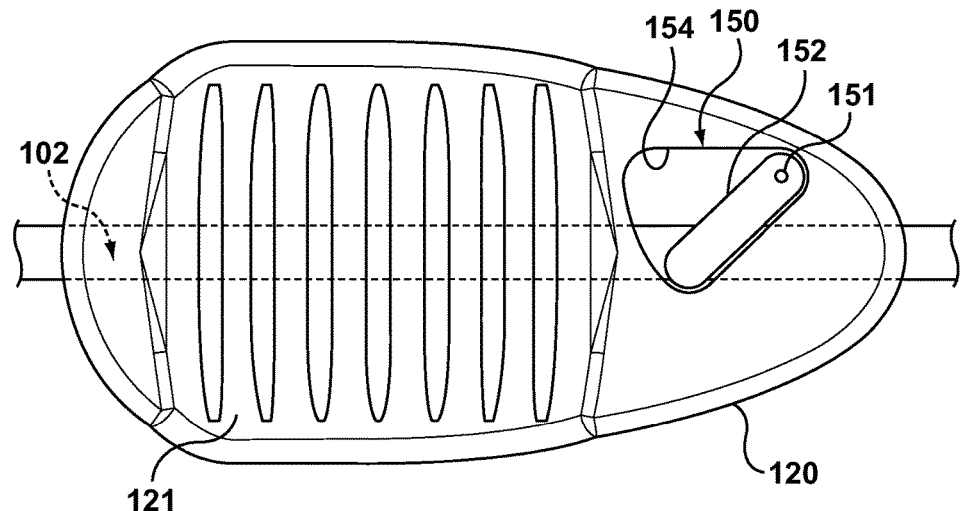

In embodiments in accordance herewith, actuation mechanism 110 includes a locking mechanism for securing or maintaining during an interventional procedure the requisite angle of deflection of the guide catheter distal end. FIGS. 8A and 8B illustrate a locking mechanism 150 in an unlocked and locked position, respectively. Locking mechanism 150 includes a latch 152 having a pivot pin 151 therethrough at a first end thereof by which the latch is operably attached to first housing portion 120. Latch 152 is pivotable about pivot pin 151 within an opening 154 of first housing portion 120 from an unengaged or unlocked position in which the latch 152 does not make contact with shaft component 102, as shown in FIG. 8A, to an engaged or locked position in which the latch 152 makes contact with and locks against shaft component 102, as shown in FIG. 8B. The frictional contact made between latch 152 and shaft component 102 is sufficient to lock a longitudinal position of first housing portion 120 relative to shaft component 102, as well as relative to second housing portion 122, such that when the actuation mechanism 110 has been manipulated to deflect the distal end of the guide catheter the locking mechanism 152 once engaged will maintain the deflected configuration of the guide catheter and will prevent the guide catheter from returning to a straight configuration until such a change in form is desired by the user.

In embodiments hereof, shaft component 102 may be formed of polymeric materials, non-exhaustive examples of which include polyethylene terephthalate (PET), polypropylene, polyethylene, polyether block amide copolymer (PEBA), polyamide, fluoropolymers, and/or combinations thereof, either laminated, blended or co-extruded. Optionally, shaft component 102 or some portion thereof may be formed as a composite having a reinforcement layer incorporated within a polymeric body in order to enhance strength and/or flexibility. Suitable reinforcement layers include braiding, wire mesh layers, embedded axial wires, embedded helical or circumferential wires, hypotubes, and the like. In an embodiment, methods of forming a catheter shaft disclosed in U.S. Pat. No. 6,375,774 to Lunn et al., which is incorporated by reference herein in its entirety, may be adapted for forming shaft component 102 as described herein.

In embodiments hereof, first and second housing portions 120, 122 of actuation mechanism 110 may be polymeric parts made by an injection molding process with the respective features of toothed rack segments 124a, 124b, pulley component 136, linear slides 128a, 128b, corresponding grooves 130a, 130b, and shaft bearing surfaces 132a, 132b, 134a, 134b, being integral features of the molded parts. Suitable polymeric materials for forming first and second housing portions 120, 122 in accordance with embodiments hereof include but are not limited to acrylonitrile butadiene styrene (ABS), polycarbonate (PC), polyphenylsulfone (PPSU), and/or combinations thereof. When first and second housing portions 120, 122 also serve as an outer casing of actuation mechanism 110, respective digit engagement surfaces 121, 123 may also be an integral feature of the molded parts. In another embodiment, a separate outer casing or outer housing may be employed within which actuation mechanism 110 is operably coupled.

In embodiments hereof, pull wire 112 may be a wire or filament of stainless steel 304, having a diameter in the range of 0.05 mm to 0.20 mm. A flat wire or ribbon having a cross-sectional area similar to the aforementioned filament may also be used. Other suitable metals or non-metallic materials may alternatively be selected for pull wire 112. The distal end of pull wire 112 is secured to an actuatable component at the distal end of the catheter. For example, the distal end of pull wire 112 can be welded to a pull band or metal sleeve within the actuatable component. In catheters such as braid-reinforced laminated guide catheters, this sleeve may be located against the distal end of the braid, and sandwiched inside the tip assembly between the inner liner and soft atraumatic tip material. The proximal end of the pull wire can be threaded between first and second housing portions 120, 122 of actuation mechanism 110 before being affixed, e.g. tied or glued to anchor point 138 once the system is taut. To complete this attachment at anchor point 138, it may be necessary to have access to the inside of the housing from the exterior, i.e. once the positioning is complete, a cover can be attached onto the housing.

In an exemplary use, guide catheter 100 in its straight configuration shown in FIG. 1 may be introduced into the vasculature via a percutaneous entry point and tracked over an indwelling guidewire through the vasculature until atraumatic tip 109 is positioned at a target site near an ostium of a vessel, such as a branch vessel, proximal of a treatment site. Actuation mechanism 110 may then be manipulated by the user to configure guide catheter 100 into a deflected configuration, such as one shown in FIG. 7, in which distal end 103 is at a suitable angle of deflection for coaxially seating atraumatic tip 109 within the ostium of the branch vessel to thereby position distal port 118 in fluid communication with the branch vessel. Once properly positioned, a treatment catheter or other interventional medical device may be introduced and tracked through guide catheter 100 to the treatment site by any suitable method known to one of ordinary skill in the art.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A catheter comprising:
an elongate shaft component extending between a proximal end and a distal end thereof;
an elongate pull wire extending within the shaft and having a proximal end and a distal end, wherein the distal end of the pull wire is secured to an actuatable component; and
an actuation mechanism disposed on a proximal portion of the shaft component with the proximal end of the pull wire being coupled thereto, wherein the actuation mechanism has a first housing portion and a second housing portion that are longitudinally translatable relative to each other and to the shaft component such that longitudinal translation of the first housing portion in a first direction relative to the shaft component with a corresponding longitudinal translation of the second housing portion in an opposite, second direction relative to the shaft component actuates the pull wire.

2. The catheter of claim 1, wherein each of the first and second housing portions of the actuation mechanism includes a toothed rack segment for engaging a pinion gear that is rotatably coupled to the proximal portion of the shaft component.

3. The catheter of claim 2, wherein the first and second housing portions include corresponding linear slides on which the first and second housing portions slide against each other.

4. The catheter of claim 3, wherein the linear slides are one of dovetail slides and rectangular slides.

5. The catheter of claim 3, wherein each of the first and second housing portions includes shaft bearing surfaces on which the first and second housing portions respectively slide against the proximal portion of the shaft component.

6. The catheter of claim 1, wherein the pull wire slidably extends from the shaft component into the actuation mechanism to engage a pulley component disposed within a proximal end of the first housing portion of the actuation mechanism with the pull wire proximal end being fixedly attached at an anchor point within a distal end of the second housing portion.

7. The catheter of claim 6, wherein the first direction is a proximal direction and the second direction is a distal direction such that when the first and second housing portions are longitudinally translated relative to each other the pull wire is simultaneously pulled proximally by the pulley component with the proximal end of the pull wire being pushed distally at the anchor point.

8. The catheter of claim 7, wherein each of the first and second housing portions of the actuation mechanism is an outer casing having an engagement surface that is configured to be engaged by a respective digit of a user's hand for longitudinally translating the first and second housing portions relative to each other.

9. The catheter of claim 1, wherein the shaft component includes a pull wire lumen within which the pull wire is slidably disposed with a distal end of the pull wire being secured therein at a distal end of the shaft component such that actuation of the pull wire by the actuation mechanism selectively deflects the distal end of the shaft component.

10. The catheter of claim 9, wherein the catheter is a guide catheter with a central lumen being sized to receive a treatment catheter therethrough, the guide catheter having a straight configuration for tracking through vasculature of a patient to a target site and a deflected configuration for positioning a distal port of the guide catheter within an ostium of a branch vessel at the target site.

11. A guide catheter comprising:
an elongate tubular component defining a central lumen from a proximal end to a distal end thereof and defining a pull wire lumen along at least a portion of a length thereof;
a pull wire extending within the pull wire lumen of the tubular component, wherein a distal end of the pull wire is secured to the distal end of the tubular component; and
a pull wire actuation mechanism slidably disposed on the tubular component and operably coupled to a proximal end of the pull wire, wherein the pull wire actuation mechanism has an upper housing that is longitudinally translatable in a first direction relative to the tubular component and a lower housing that is longitudinally translatable in an opposite, second direction relative to the tubular component to actuate the pull wire to selectively deflect the distal end of the tubular component.

12. The guide catheter of claim 11, wherein the guide catheter has a straight configuration for tracking through vasculature of a patient to a target site and a deflected configuration for positioning a distal port of the guide catheter within an ostium of a branch vessel at the target site.

13. The guide catheter of claim 12, wherein the pull wire actuation mechanism includes a locking mechanism for securing the deflected configuration.

14. The guide catheter of claim 11, wherein each of the upper and lower housings of the pull wire actuation mechanism includes a toothed rack segment for engaging a pinion gear that is rotatably coupled to the tubular component.

15. The guide catheter of claim 14, wherein the upper and lower housings include corresponding linear slides on which they slide against each other.

16. The guide catheter of claim 15, wherein the linear slides are one of dovetail slides and rectangular slides.

17. The guide catheter of claim 15, wherein each of the upper and lower housings includes bearing surfaces on which the upper and lower housings respectively slide against the tubular component.

18. The guide catheter of claim 11, wherein the pull wire slidably extends from the pull wire lumen of the tubular component into the pull wire actuation mechanism to engage a pulley component disposed within a proximal end of the upper housing with the pull wire proximal end being fixedly attached at an anchor point within a distal end of the lower housing.

19. The guide catheter of claim 18, wherein the first direction is a proximal direction and the second direction is a distal direction such that when the upper and lower housings are longitudinally translated relative to each other the pull wire is simultaneously pulled proximally by the pulley component with the proximal end of the pull wire being pushed distally at the anchor point.

20. The guide catheter of claim 11, wherein each of the upper and lower housings is an outer casing of the pull wire actuation mechanism having an engagement surface that is configured to be engaged by a respective digit of a user's hand for longitudinally translating the upper and lower housings in their respective first and second directions relative to the tubular component.

* * * * *